United States Patent [19]

van Zon et al.

[11] 4,288,333

[45] Sep. 8, 1981

[54] DISSOLVING BARIUM SULFATE SCALE WITH AQUEOUS SOLUTIONS OF SALTS OF PHOSPHOMETHYL AND AMINO-SUBSTITUTED MACROCYCLIC POLYETHERS

[75] Inventors: Arie van Zon; Feike de Jong; Gerridina J. Torny-Schutte, all of Amsterdam, Netherlands

[73] Assignee: Shell Oil Company, Houston, Tex.

[21] Appl. No.: 91,009

[22] Filed: Nov. 5, 1979

[30] Foreign Application Priority Data

Jun. 29, 1979 [GB] United Kingdom ............... 22689/79

[51] Int. Cl.[3] .......................... C02F 5/14; E21B 43/25
[52] U.S. Cl. .................... 252/8.55 B; 134/2; 134/42; 166/312; 252/82; 252/86; 260/338
[58] Field of Search ...... 252/8.55 B, 82, 86, 252/87; 166/305 R, 312; 134/2, 22 R, 22 C, 42

[56] References Cited

U.S. PATENT DOCUMENTS

| | | | |
|---|---|---|---|
| 3,738,937 | 6/1973 | Kautsky | 134/2 |
| 3,966,766 | 6/1976 | Lehn | 260/338 X |
| 3,996,062 | 12/1976 | Frost et al. | 134/2 |
| 4,030,548 | 6/1977 | Richardson et al. | 134/2 X |
| 4,190,462 | 2/1980 | De Jong et al. | 252/8.55 X |
| 4,215,000 | 7/1980 | De Jong et al. | 252/8.55 |

FOREIGN PATENT DOCUMENTS 1304367  6/1973  United Kingdom .

OTHER PUBLICATIONS

Lehn, *Accounts of Chemical Research,* vol. 11, 1978, pp. 49–57.

*Primary Examiner*—Herbert B. Guynn

[57] ABSTRACT

Barium sulfate scale can be removed from remote locations such as those in or around the borehole of a well extending into a subterranean earth formation by contacting the scale with an aqueous solution consisting essentially of water, a monovalent cation salt of a macrocyclic polyether containing at least two nitrogen-linked phosphomethyl groups and enough monovalent basic compound to provide a solution pH of about 8.

5 Claims, No Drawings

DISSOLVING BARIUM SULFATE SCALE WITH AQUEOUS SOLUTIONS OF SALTS OF PHOSPHOMETHYL AND AMINO-SUBSTITUTED MACROCYCLIC POLYETHERS

BACKGROUND OF THE INVENTION

The present invention relates to well treating uses of phosphomethyl and amino-substituted macrocyclic polyethers, to processes for their preparation, and to complexes formed from them. The present invention further relates to compositions, especially aqueous compositions, containing such polyethers which can be used as cleaning agents, especially for cleaning a well penetrating an underground formation and optionally cleaning formation parts in the vicinity of the said well. Finally, the present invention also relates to cleaning processes using such macrocyclic polyethers.

Synthetic macrocyclic polyethers (often referred to as "crown ethers") are of great interest in that they contain intra-molecular cavities which are fit to accommodate alkali metal or alkaline earth metal ions depending on the particular shape of the polyether employed. Therefore, salts of alkaline earth metals which are substantially insoluble in water can be solubilized by aqueous solutions of such polyethers. It is also possible to dissolve such salts in organic solvents such as benzene or toluene in the presence of such polyethers. Reference is made in this respect to British Patent Specification No. 1,304,367 and to Acc. of Chem. Res., Volume 11 (1978) pages 49-57.

Various well treating procedures for removing various types of scales with aminopolyacetic acid salt chelating agents, such as EDTA (ethylenediaminetetraacetic acid), are known. For example, U.S. Pat. No. 2,396,938 (filed in 1944) describes removing boiler scale with aqueous solutions of such a chelant and an alkali metal hydroxide. U.S. Pat. No. 2,802,788 (filed in 1952) describes a radiator cleaning composition in which such a chelant salt is included in an aqueous solution along with an inorganic chelant, e.g., sodium tripolyphosphate. U.S. Pat. No. 3,308,065 (filed in 1963) describes a substantially one-pore volume treatment for removing calcium sulfate-containing scale with an ammoniated or aminated chelant, e.g., an ammonium salt of EDTA. U.S. Pat. No. 3,660,287 (filed in 1967) describes a similar treatment for dissolving calcium sulfate-containing scale with a mixture of an EDTA salt and water soluble inorganic carbonate salt. While the above processes were consistent in utilizing an amount of solution which about filled one pore volume of the region within which the scale was to be removed and using a concentration of chelant such that that volume of the solution contained a stoichiometric excess relative to the amount of scale to be dissolved, U.S. Pat. Nos. 2,877,848 and 4,030,548 relate to using relatively dilute solutions. The U.S. Pat. No. 4,030,548 describes the tendancy for relatively concentrated EDTA solutions to become quickly saturated with a Ba-EDTA complex and suggests a one-through-dynamic wash treatment with enough solution to gradually remove the solid.

Numerous monocyclic and bicyclic macrocyclic polyethers and their tendancies to chelate with alkaline earth metals and to dissolve salts of such metals are disclosed in "Tetrahedron Letters" No. 34 (1969), pages 2889-2892. U.S. Pat. Nos. 3,888,877 and 3,966,766 relate to such polyethers and their general utility as chelating agents.

One co-pending patent application Ser. No. 951,701, filed Oct. 16, 1978 by F. DeJong, G. J. Torny-Schutte and D. N. Reinhoudt, now U.S. Pat. No. 4,215,000, relates to dissolving a barium sulfate solid from a remote location into which fluid can be flowed by contacting that solid with an aqueous solution consisting essentially of: water, a bicyclic macrocyclic polyether, a proportion of alkali metal salt of an organic acid which is less than that of the polyether but is sufficient to catalytically increase the rate of barium solid dissolving by the polyether, and enough dissolved alkaline inorganic alkali metal or ammonium compound to provide a solution pH of at least about 8.

Another co-pending patent application by the same inventors, Ser. No. 003,155, filed Jan. 15, 1979, now U.S. Pat. No. 4,190,462, relates to a process comprising contacting the surfaces to be cleaned with an aqueous solution consisting essentially of water, a monovalent cation salt of a monocyclic macrocyclic polyether containing at least two nitrogen-linked carboxymethyl groups and enough dissolved alkaline inorganic alkali metal or ammonium compound to provide a solution pH of at least about 8. That polyether contains an intramolecular cavity or crypt which is selectively receptive to multivalent cations. And, the aqueous solution is both capable of relatively rapidly dissolving barium sulfate scale and free of any bicyclic macrocyclic polyether.

SUMMARY OF THE INVENTION

The present invention relates to well treating processes and to novel phosphomethyl and amino-substituted macrocyclic polyethers which are useful in those processes. Those polyethers have the formula:

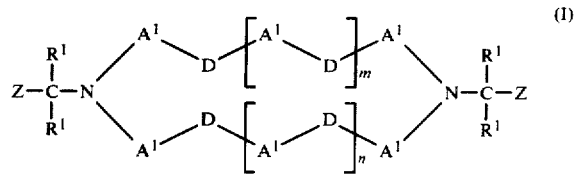

(I)

wherein each A¹(which may be the same or different) represents a hydrocarbon radical of up to 12 carbon atoms and each D (which may be the same or different) represents an oxygen or sulphur atom or a hydrocarbon radical having up to 6 carbon atoms or a group N-R (R representing a hydrogen atom or a hydrocarbon radical having up to 12 carbon atoms, a hydrocarbon sulphonyl radical having up to 12 carbon atoms, an alkoxycarbonyl-methylene radical having up to 4 carbon atoms or a carboxymethylene radical), at least 2 of the said D members representing an oxygen or a sulphur atom or a group N-R, and each R¹(which may be the same or different represents a hydrogen atom, an alkyl group having up to 6 carbon atoms or a carboxy group, m and n are whole numbers from 0 to 5 inclusive and Z represents a group

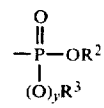

wherein y is 0 or 1 and $R^2$ and $R^3$ (which may be the same or different) represent a hydrogen atom or an alkyl group and the corresponding salts.

It has been found that the presence of the phosphomethyl groups which provide just one carbon atom between each of the bridging-nitrogen atoms of the macrocyclic ring and the adjacent phosphorus atoms, is essential for the performance of the salts of the present P and N-containing macrocyclic polyethers (according to formula I) as cleaning agents. For example, when an otherwise similar polyether is modified by replacing the two phosphomethyl groups

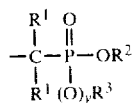

wherein y is 0 or 1 with (a) 2-phosphonoethyl groups (containing two carbon atoms between the phosphorus atom and the bridging nitrogen atom of the macrocyclic ring) or (b) $-CH_2-SO_3H$ groups (containing one carbon atom but a sulphur atom rather than a phosphorus atom), the salts of the macrocyclic polyethers thus obtained exhibit insufficient complexing ability to dissolve water-insoluble alkaline-earth metal salts such as barium sulphate.

Preferred compounds according to the general formula I are those wherein each $A^1$ which may be the same or different represents a hydrocarbon radical having in the range of from 2 to 6 carbon atoms or a 1,2-phenylene radical, D represents an oxygen or sulphur atom or a group N-R (R representing a hydrogen atom, an alkyl group of up to 6 carbon atoms, a hydrocarbon sulphonyl radical of up to 6 carbon atoms or an alkoxycarbonyl-methylene radical having up to 4 carbon atoms or a carboxymethylene radical); at least 4 of the said D members representing oxygen atoms and/or groups N-R; and each $R^1$ which may be the same or different represents a hydrogen atom, an alkyl group having up to 4 carbon atoms or a carboxy group; m and n are 1 or 2; and Z represents a group

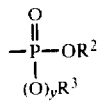

wherein y is 0 or 1 and $R^2$ and $R^3$ which may be the same or different represent a hydrogen atom or an alkyl group of up to 6 carbon atoms and the corresponding salts.

More preferred compounds according to the general formula I are those wherein each $A^1$ which may be the same or different represents an ethylene, diethylene, triethylene or tetraethylene radical, particularly an ethylene radical; D represents an oxygen atom or a group N-R (R representing an alkyl group of up to 4 carbon atoms, particularly a methyl group, a hydrocarbon sulphonyl radical of up to 4 carbon atoms or a methoxy- or ethoxycarbonyl radical); at least 4 of the said D members representing an oxygen atom; and each $R^1$ which may be the same or different represents a hydrogen atom or a methyl or ethyl group; m and n are 1 or 2; and Z represents a group

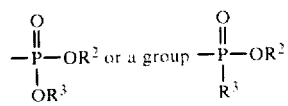

wherein $R^2$ and $R^3$ both represent a hydrogen atom, and the corresponding salts.

Most preferred compounds according to the general formula I are those wherein $A^1$ represents an ethylene radical; D represents an oxygen atom; and each $R^1$ which may be the same or different represents a hydrogen atom or a methyl or ethyl group; m and n are both 1; and Z represents a group

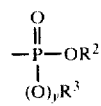

wherein y is 0 or 1, and $R^2$ and $R^3$ both represent a hydrogen atom, and the corresponding salts.

Examples of compounds according to the present invention are:

1,10-bis(phosphonomethyl)-1,10-diaza-4,7,13,16-tetraoxacyclooctadecane;

1,10-bis(phosphono(alpha-methyl)methyl)-1,10-diaza-4,7,13,16-tetraoxacyclooctadecane;

1,10-bis(phosphinicomethyl)-1,10-diaza-4,7,13,16-tetraoxacyclooctadecane;

1,10-bis(phosphinico(alpha-methyl)methyl)-1,10-diaza-4,7,13,16-tetraoxacyclooctadecane;

1,10-bis(phosphinico(alpha,alpha-dimethyl)methyl)-1,10-diaza-4,7,13,16-tetraoxacyclooctadecane and esters and/or salts thereof.

The present invention also relates to complexes formed from a compound according to the general formula I, or from the corresponding salts, with cations which are compatible with such compounds. The expression "compatible" as used herein is meant to denote that a macrocyclic polyether according to the general formula I is capable of accommodating the cation in the intramolecular cavity of the polyether molecule. It will be appreciated that when reference is made to "the corresponding salts" of the compounds according to the general formula I in connection with their complexing ability those salts are meant whose cations are not competitive or are hardly competitive with the cation(s) to be complexed with the polyether. In other words, when compounds according to the general formula I are used in the salt-form then the cations of those salts should have no, or hardly any, ability of being accommodated by the polyether concerned.

The present invention also relates to processes for the preparation of macrocyclic polyethers according to the general formula I or esters or salts thereof. The compounds according to the general formula I can be prepared by reacting a macrocyclic polyether according to the general formula:

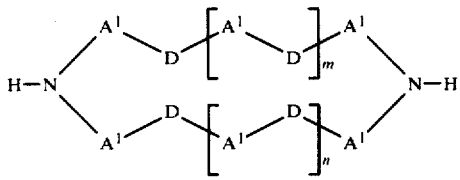
(II)

wherein $A^1$, D, m and n have the meansing as defined hereinbefore with hypophosphorous acid or partial alkyl esters thereof in the presence of a compound according to the general formula:

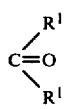
(III)

wherein each $R^1$ (which may be the same or different) has the meaning as defined hereinbefore, and optionally converting the acid obtained into the corresponding ester or salt.

This process according to the present invention can be carried out conveniently by dissolving a compound according to the general formula II (e.g. 1,10-diaza-4,7,13,16-tetraoxacyclooctadecane) in water preferably in the presence of a mineral acid such as hydrochloric or hydrobromic acid or sulphuric acid in order to facilitate the reaction followed by the addition of the required amount of hypophosphorous acid in aqueous solution and the required carbonyl-compound. If desired a slight excess of the hypophosphorous acid can be used. When using partial alkyl esters such as mono- or dialkyl phosphites or mono-alkylhypophosphites, the reaction should be carried out in the absence of mineral acids.

The above-mentioned process can be carried out conveniently at temperatures in the range of from 10° C. to 120° C. Preference is given to temperatures in the range of from 40° C. to 110° C.

The compounds according to the general formula I wherein y=1 can also be prepared by reacting a compound according to the general formula II with a compound according to the general formula:

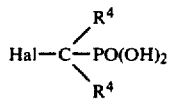
(IV)

wherein Hal represents a chlorine, bromine or iodine moiety and each $R^4$ which may be the same or different represents a hydrogen atom or an alkyl group of up to 6 carbon atoms, in the presence of a base. Preferably, the reaction should be carried out in the presence of at least two moles of base per mole of compound according to the general formula II. Suitable bases comprise lithium hydroxide, sodium hydroxide, potassium hydroxide, and alkyl-substituted ammonium compounds such as tetra-alkyl-ammonium compounds. 2-Chloromethylphosphonic acid is a suitable starting material for the preparation of 1,10-bis(phosphonomethyl)-1,10-diaza-4,7,13,16-tetraoxacyclooctadecane.

It was found convenient to heat the reaction mixture prior to the addition of the compound according to the general formula III. After adding the compound according to the general formula III either in an aqueous solution (when both $R^1$ represent a hydrogen atom) or as such (e.g. when both $R^1$ represent a methyl group) the reaction mixture is refluxed for a couple of hours.

The reaction mixture can be worked up by methods known in the art. The acid obtained can be converted into a corresponding ester by methods known in the art, e.g., by treatment with an ortho ester, a trialkylphosphite or diazomethane. The corresponding salts can be obtained by adding a base, preferably a base whose cation is not, or is hardly compatible with the complexing action of the macrocyclic polyether. Examples of suitable bases comprise lithium hydroxide, sodium hydroxide, potassium hydroxide, ammonia as well as alkyl-substituted ammonium hydroxides. Very good results can be obtained using lithium hydroxide as the lithium salts of the macrocyclic polyethers according to the general formula I are very suitable in aqueous solutions for the dissolution of virtually water-insoluble inorganic salts.

It should be noted that also inner salts of the macrocyclic polyethers according to the general formula I, i.e, quaternary ammonium salts obtained by acidifying the macrocyclic polyether according to the general formula I, comprising one or more macrocyclic polyethers according to the general formula I.

The ability of macrocyclic polyethers to dissolve salts whose cations are compatible with the macrocyclic polyethers is well-known and based on their remarkable capability to form complexes with alkali- and alkaline-earth metal ions by holding them entrained within the framework formed by the hetero atoms occurring in the ring structure. This is of great interest as the complexes formed are generally readily soluble in polar solvents such as water, lower alkanols, ketones, halogenated alkanes and to a lesser extent in aromatic hydrocarbons such as benzene and toluene. The complexes are normally formed by dissolving the macrocyclic compound and the salt to be dissolved in a suitable solvent such as water, acetone, methanol or dichloromethane, if required under heating. Depending on the solubility of the complex concerned, a dissolved complex will be obtained or the complex will crystallize as such.

Of particular interest are those compositions which are capable of dissolving salts which are substantially insoluble in water such as barium sulphate, barium carbonate, calcium sulphate and calcium carbonate. The presence of one or more of such salts as deposits on surfaces such as reaction flasks, vessels, pipelines, casings, tubings and bore-heads is undesired in that they tend to increase fouling of the equipment to an unacceptably high level.

Especially in the process of recovering oil from an oil-containing subterranean formation via a well penetrating the formation, fouling of the tubular equipment in the well with barium sulphate scale may cause undesirable low production rates. Further, precipitation of barium sulphate on the walls of the pore space during the oil recovery operations will cause permeability decrease in the formation pore space which lowers production rates.

Barium sulphate scale can be deposited or formed from pressure and/or temperature changes in the flow of oil, or by the co-mingling of individually stable waters, of which one is rich in sulphate ions and the other in barium ions. Also fine barite particles that have been included in the drilling mud applied in drilling the well and that have invaded the pay-zone of the formation cause a permanent impairment of the well productivity which requires cleaning of the formation parts.

As the time during which an oil well is being cleaned and out of operation should be as short as possible, the barium sulphate scale must dissolve rapidly into the aqueous composition giving a barium complex which is highly soluble in water. In addition a high loading of the active ingredient is desirable. Aqueous compositions according to the present invention which contain salts of the 10,10bis(phosphonomethyl)-1,10-diaza-4,7,13,16-tetraoxacyclooctadecanes do contribute substantially to the dissolution of barium sulphate solids.

The concentration in which the salt of the macrocyclic polyether according to the general formula I is present in the aqueous solution is not critical. This concentration is suitably taken substantially equivalent to the saturation concentration of the complex of barium with the polyether in the aqueous composition under the prevailing conditions. Suitably, the concentration of the salt of the macrocyclic polyether is at least 0.01 mol/l and preferably higher than 0.05 mol/l, for example 0.3 mol/l.

The aqueous composition according to the present invention will normally be alkaline. It will be clear that protonation of the nitrogen bridging atoms in the macrocyclic polyether according to the general formula I will reduce its tendency to form barium complexes. Thus, the higher the pH, the higher the unprotonated portion of the macrocyclic polyether will become and, consequently, the higher the extent to which this macrocyclic polyether can be loaded up with barium ions. In view of this, the aqueous composition preferably has a pH of at least 8, more preferably of at least 10, and particularly a pH in the range of from 10 to 11.5. The unprotonated portion of the macrocyclic polyether can be increased by incorporating a base into the aqueous composition, preferably a base whose cation is hardly competitive, if at all, with the barium ion to be complexed by the macrocyclic polyether according to the general formula I; an example of a base that is not, or hardly competitive is lithium hydroxide.

It will be appreciated that the aqueous composition according to the present invention can be obtained in various ways. It is possible, for instance, to dissolve the salt of a macrocyclic polyether according to the general formula I in water, whether or not in the presence of an additional base. It is also possible and quite convenient to obtain an aqueous solution of an acid salt of a macrocyclic polyether according to the general formula I— e.g. the mono- or bis-hydrochloric acid salt of 1,10-di(-phosphonomethyl)-1,10-diaza-4,7,13,16-tetraoxacyclooctadecane-, which solution is then treated with at least an equivalent amount of a base, preferably a base whose cation is hardly compatible, if at all, with the macrocyclic polyether structure. Thus, at least 4 equivalents of base (e.g. lithium hydroxide) should be used to convert a bishydrochloric acid salt as referred to hereinabove into a salt of a macrocyclic polyether according to the present invention. Good results have been obtained using up to 16, preferably up to 6 equivalents of base.

Another interesting method of obtaining an aqueous composition according to the present invention comprises the in situ production of the salts of the macrocyclic polyethers by reacting the corresponding macrocyclic polyether with a compound according to the general formula III and hypophosphorous acid or with a compound according to the general formula IV in the presence of an excess of a base. It is also possible to use the crude reaction mixture obtained in the synthesis of the salts of the macrocyclic polyethers according to formula I.

The cation of the salt of the macrocyclic polyether present in the aqueous composition may be any cation, for example, a lithium, sodium, potassium or an ammonium, or alkyl substituted ammonium-ion, for example a tetraalkyl substituted ammonium ion. This cation is preferably not, or hardly competitive with the barium ion to be complexed with the macrocyclic polyether according to formula I. Preference is given to the use of lithium salts.

The aqueous composition used in the process according to the present invention may also contain well-treating or cleaning solution additives which are compatible with the composition. Such additives include, for example, surfactant materials. These surfactant materials may be ionic or nonionic. Examples are alkali metal salts of alkyl aryl sulphonates such as sodium dodecylbenzene sulphonote, alkali metal salts of sulphates of fatty alcohols such as sodium lauryl sulphate and materials having a polyoxyethylene chain. The surfactant material may be present in the composition in a concentration in the range of from, for example, 1 to 3% by weight.

The contact time for dissolving a barium sulphate solid with the aqueous composition will vary not only with the conditions but also with the relative proportions of the constituents in the composition and will generally be in the range of from 1 minute to 3 hours; for example from 5 minutes to 1.5 hours.

In general, when using an aqueous composition according to the present invention for dissolving a barium sulphate solid, there is no need to adopt temperatures substantially above ambient temperature. Temperatures as low as 10° to 20° C. have been found satisfactory. However, the relatively high temperature (say 30°-70° C. or higher) prevailing in an oil producing formation into which a production well penetrates, greatly enhances the dissolution of the solid. As discussed hereinbefore, this is of great advantage for the in situ preparation of the salts of the macrocyclic polyethers according to formula I.

It will be appreciated that aqueous compositions according to the present invention can also be applied when other types of scale and/or compounds whose ions can be accommodated by the salts of amcrocyclic polyethers according to formula I are present in wells and/or formation parts in the vicinity of said wells. The aqueous compositions can be suitably applied when for instance, calcium sulphate solid is also present in the well and/or the formation parts in the vicinity of said well.

It should be noted that the compounds according to the general formula I wherein $Y = 0$ ("phosphinico compounds") may be converted into the corresponding "phosphono compounds" ($Y = 1$) under oxidizing conditions. Such conditions, e.g. the presence of oxygen or air and/or metal ions which can catalyse oxidation reactions may prevail when (aqueous) compositions comprising phosphinico compounds are used as cleaning agents, especially for cleaning wells penetrating underground formations. It is likely that under such conditions a mixture of phosphinico and phosphono compounds will cause the complexation of barium and/or calcium ions. It is also possible that the phosphinico compounds disproportionate to some extent under the prevailing conditions to give a phosphine and a phosphonic acid in a 1:2 ratio.

The present invention is illustrated by means of the following Examples. The experiments described below to test the dissolving-capacities of several aqueous compositions were carried out in a cylindrical glass vessel having a height of 2.5 cm and an internal diameter of 0.8 cm and containing five stainless steel balls with a diameter of 0.32 cm. The vessel was charged with the starting materials and then fixed lengthwise to a horizontal shaft parallel to its central axis. The shaft was rotating at a speed of 180 revolutions per minute. The temperature of the vessel was 20° C. unless otherwise indicated.

EXAMPLE 1

(a) 1,10-Bis(phosphonomethyl)-1,10-diaza-4,7,13,16-tetraoxacyclooctadecane was prepared as follows. To a solution of 1.31 g (5 mmol) 1,10-diaza-4,7,13,16-tetraoxacyclooctadecane in 4 ml of a mixture of conc. HCl/H$_2$O (1:) was added 2.37 ml of 30% H$_3$PO$_3$ (10 mmol). The reaction mixture was heated to 100° C. and 1.6 ml of 37% formaldehyde was added after which the reaction mixture obtained was refluxed during 4 hours. Thereafter the reaction mixture was evaporated until dryness and the residue treated with dry ethanol (25 ml) from which 1.4 g mono HCl salt of 1,10-bis(phosphonomethyl)-1,10-diaza-4,7,13,16-tetraoxacyclooctadecane (2.88 mmol, 58% yield) precipitated. From the mother liquor a further crop of 0.64 g could be isolated giving a total yield of 2.04 g (4.19 mmol, 84% yield).

The mono HCl salt which had precipitated had m.p. 258°–260° C.

Analysis for the mono HCl salt (C$_{14}$H$_{33}$ClN$_2$O$_{10}$P$_2$): Calculated: C:34.5; H 6.8; N 5.8; O 32.9; Cl:7.3; P 12.8%. Found: C:33.8; H 6.6; N 5.7; O 33.0; Cl:7.2; P 13.4%.

The P.M.R., $^{13}$C NMR and —P NMR-data (all recorded using D$_2$O as the solvent) were in accordance with the expected structure.

(b) The vessel was charged with barium sulphate (0.45 mmol), water (1.5 ml), 1,10-bis(phosphonomethyl)-1,10-diaza-4,7,13,16-tertaoxacyclooctadecane (0.15 mmol) and so much lithium hydroxide that the aqueous solution in the vessel had a pH of 11. After 30 minutes of rotation the suspension was allowed to separate by settling. A sample drawn from the aqueous layer contained dissolved barium sulphate (11.1 g/l). Hence the lithium salt of 1,10-bis(phosphonomethyl)-1,10-diaza-4,7,13,16-tetraoxacyclooctadecane had been used with an efficiency of [11.1/(233.2×0.1)]×100=47.8% After 3 hours of rotation the efficiency had become 54.1% and after 24 hours of rotation the efficiency was 65.2% (15.2 g barium sulphate dissolved per liter) determined by SO$_4{}^{--}$-analysis. Within the limits of experimental error the same results were obtained by SO$_4{}^{--}$ as well as by Ba$^{++}$ analysis.

(c) The experiment described under (b) was repeated at a temperature of 70° C. After 24 hours of rotation the efficiency of the lithium salt of 1,10-bis(phosphonomethyl)-1,10-diaza-4,7,13,16-tetraoxacyclooctadecane (0.37 mmol) was 78% determined by SO$_4{}^{--}$ analysis (18.2 g barium sulphate dissolved per liter).

(d) The vessel was charged with water (1.2 ml), natural barite (524 mg, grain size 4 mm) and 1,10-bis(phosphonomethyl)-1,10-diaza-4,7,13,16-tetraoxacyclooctadecane (0.37 M). Then so much lithium hydroxide was added that the pH of the aqueous liquid had a value of 11. The natural barite contained the following compounds:

| Compound | % w | Compound | % w |
|---|---|---|---|
| BaSO$_4$ | 80 | Fe$_2$O$_3$ | 3 |
| SiO$_2$ | 13 | SrSO$_4$ | 2 |

Hence, 1.8 mmol of barium sulphate was present in the flask. After 97.5 hours' rotation the liquid contained dissolved barium sulphate in a concentration of 0.088 M (20.9 g barium sulphate dissolved per liter). Thus the phosphono compound had been used with an efficiency of (0.088/0.37)×100=24%.

(e) The experiment described under (d) was repeated at a temperature of 70° C. After 96 hours' rotation the efficiency of the lithium salt of the phosphono compound amounted to 53% as determined by SO$_4{}^{--}$ analysis.

Comparative Experiment A

This experiment differed from that described in Example 1b in that the phosphomethyl compound was replaced by 1,10-bis(2-phosphonoethyl)-1,10-diaza-4,7,13,16-tetraoxacyclooctadecane (0.1 M). This compound was obtained by reacting 1,10-diaza-4,7,13,16-tetraoxacyclooctadecane with ethylene oxide, heating the 2-hydroxy ethyl compound obtained with thionyl chloride and converting the 2-chloro ethyl compound obtained with the triethyl ester of phosphorous acid followed by acid hydrolysis. The sample drawn after 20 hours' rotation from the aqueous layer contained dissolved sulphate in an amount of 1.5 g/l. No barium ions could be detected in the aqueous layer indicating that most of the complexed barium was present in the vessel as an unwanted solid. This clearly indicates that the presence of an additional carbon atom between the bridging nitrogen atom of the macrocyclic ring and the phosphorous atom virtually destroys the complexing-/dissolving ability.

Comparative Experiment B

This experiment differed from that described in Example 1b in that the phosphomethyl compound was replaced by 1,10-bis(2-ethylmonophosphate)-1,10-diaza-4,7,13,16-tetraoxacyclooctadecane (0.1 M). This compound was obtained by reacting the 2-hydroxyethyl compound mentioned in Comparative Experiment A with chlorophosphoric acid diphenyl ester in the presence of sodium hydride in tetrahydrofuran followed by hydrogenolysis over platinum in acetic acid. The sample drawn after 20 hours' rotation from the aqueous layer contained dissolved barium and dissolved sulphate in amounts of 0.05 and 0.8 g/l, respectively, calculated as barium sulphate, indicating that most of the complexed barium was present in the vessel as an unwanted solid. Hence the 1,10-bis(2-ethylmonophosphate)-1,10-diaza-4,7,13,16-tetraoxacyclooctadecane had been used with an efficiency of [0.05/(2.33.2×0.1)]×100=0.2% on barium of [0.8/(233.2×0.1)]×100=3.5% on sulphate.

Comparative Experiment C

This experiment differed from that described in Example 1b in that the phosphomethyl compound was replaced by 1,10-bis(sulphonomethyl)-1,10-diaza- 4,7,13,16-tetraoxacyclooctadecane (0.1 M). This compound was obtained by reacting 1,10-diaza-4,7,13,16-tetraoxacyclooctadecane with sodium sulphite and 37% formaldehyde (see example 2a). The sample drawn after 24 hours' rotation contained dissolved barium in an amount of 0.2 g/l, determined by $Ba^{++}$ analysis. Hence the efficiency of the lithium salt of the sulphonomethyl compound was 0.9%, which clearly indicates that the complexing/dissolving ability is virtually destroyed whrn the phosphonate is replaced with the sulphonate.

EXAMPLE 2

(a) 1,10-Bis(phosphinicomethyl)-1,10-diaza-4,7,13,16-tetraoxacyclooctadecane was prepared by adding to a solution of 1.31 g (5 mmol) 1,10-diaza-4,7,13,16-tetraoxacyclooctadecane in 4 ml conc. $HCl/H_2O$ (1:) 1.06 ml 50% hypophosphorous acid (10 mmol). The reaction mixture was heated until reflux followed by the addition of 1.6 ml 37% formaldehyde (20 mmol). The reaction mixture obtained was refluxed during 6 hours. After cooling the pH was adjusted with LiOH to pH 6.7. A dample of 1.3 ml was drawn from the reaction mixture (see Example 2b) and the resulting product was then purified over an ion-exchange column (IR 120(H)). The resultant phosphinico-compound containing fractions were collected and boiled down. This resulted in 1.45 g (2.95 mmol; 74% yield) of the di-HCl salt of 1,10-bis(phosphinicomethyl)1,10-diaza-4,7,13,16-tetraoxacyclooctadecane, a hygroscopic, frothy product.

Analysis for the di-HCl-salt ($C_{14}H_{34}Cl_2N_2O_8P_2$): Calculated: C:34.2; H:7.0; N:5.7; O:26.0; P:12.6; Cl:14.4% Found: C:31.0; H:6.2; N:4.7; O:27.3; P:10.6; Cl:15.3%

(metal containing residue of 7.6% was found, likely from entrained LiCl). The PMR, $^{13}C$ NMR and $^{31}P$ NMR-data (all recorded using $D_2O$ as the solvent) were in accordance with the expected structure.

(b) The vessel was charged with barium sulphate (0.3 mmol/ml) and the sample referred to in Example 2a (1.3 ml) which had been made alakline with lithium hydroxide to pH=11 and diluted to 10 ml. The concentration of the phosphinico compound was 0.1 M. After 24 hours of rotation the suspension was allowed to separate by settling. A sample drawn from the aqueous layer contained barium sulphate (4.4 g/l). Hence, the lithium salt of the phosphinico compound had been used with an efficiency of $[4.4(233.2 \times 0.1)] \times 100 = 18.9\%$

EXAMPLE 3

(a) 1,10-Bis(phosphinico(alpha-methyl)methyl)-1,10-diaza-4,7,13,16-tetraoxacyclooctadecane was prepared in the manner described in Example 2a using acetaldehyde (0.6 ml, about 10 mmol in 1.5 ml water) instead of formaldehyde. The conversion, followed by NMR-analysis was about 35%. The product was directly treated with lithium hydroxide (see Example 3b).

The compound was characterized by $^1H$, $^{13}C$ and $-P$ NMR in $D_2O$.

The following signals were assigned: $^1H$ NMR in $D_2O/HCl$ ($H_2O$ as 0 ppm): $\delta$: $-0.98$ (t); $-1.08$ (m) and $-3.44$ (m). $^{13}C$ NMR in $D_2O$:

$\delta = 73.2$ (ethylene carbon atoms between oxygen atoms);

66.6 (carbon atoms of an ethylene group next to the oxygen atom and between an oxygen and a nitrogen atom);

54.6 (carbon atoms of an ethylene group next to the nitrogen atom and between an oxygen and a nitrogen atom);

and 10.7 (carbon atom of the alpha methyl group). Also a coupling constant of 10 Hz (C-C-P) was recorded. $^{31}P$ NMR in $D_2O$: $\delta - 36.8$ ppm ext. reference 85% $H_3PO_4$).

(b) The reaction mixture obtained in the experiment described in Example 3a (8 ml) was made alkaline with lithium hydroxide to pH=11 and diluted to 16.5 ml (thus obtaining the alpha-methyl phosphinicocompound in a concentration of 0.1 M). After 24 hours of rotation with 0.3 mmol/ml barium sulphate the suspension was allowed to separate by settling. A sample drawn from the aqueous layer contained dissolved barium sulphate (2.1 g/l). Hence, the lithium salt of the alpha-methyl phosphinico compound had been used with an efficiency of 8.9%. It should be noted that unreacted starting material (1,10-diaza-4,7,13,16-tetraoxacyclooctadecane) has also some ability to complex barium-ions under the prevailing conditions. It was found that the unreacted starting material could dissolve no more than 0.2 g barium sulphate per liter under these conditions.

(c) The experiment described in Example 3a was repeated using phosphorous acid (30%) rather than hypophosphorous acid. The reaction was rather slow as followed by NMR-analysis and at 10% conversion (NMR-analysis) lithium hydroxide was added until the pH of the reaction mixture was 11. The total (diluted) reaction mixture was 8 ml which did not contain more than 0.5 mmol of 1,10-bis(phosphono(alphamethyl)methyl)-1,10-diaza-4,7,13,16-tetraoxacyclooctadecane. This mixture was used in the manner described hereinbefore to dissolve barium sulphate. After 24 hours' rotation and working up, 0.66 g of barium sulphate had dissolved per liter (uncorrected for starting material) amounting to an efficiency of about 4.5%.

(d) The experiment described in Example 2a was repeated using acetone (1.2 g, 20 mmol) in 1.5 ml $H_2O$ instead of formaldehyde. The reaction was followed with NMR-analysis and a conversion of 10% of the starting material into 1,10-bis(phosphinico(alpha,alpha-dimethyl)methyl)-1,10-diaza-4,7,13,16-tetraoxacyclooctadecane was calculated based on the following $^1H$, $^{13}C$, and $^{31}P$ NMR signals: $^1H$ NMR in $D_2O/HCl$ ($H_2O$ as 0 ppm): $\delta = -1.02$; $-1.12$ (ring protons); $-3.54$ d, apha methyl groups).

$^{13}C$ NMR in $D_2O$: in addition to signals attributed to the ring also=25.3 (alpha methyl groups, d). A coupling constant of 10 Hz (C-C-P) was recorded. $^{31}P$ NMR in $H_2O/D_2O/HCl$: $-40.5$ ppm (ext. reference 85% $H_3PO_4$).

The reaction mixture was used for testing in the manner described in Example 3c. After 24 hours' rotation and working up, 0.55 g of barium sulphate had dissolved per liter (uncorrected for starting material) amounting to an efficiency of about 3.2%.

EXAMPLE 4

To a solution of 100 mg 1,10-bis(phosphonomethyl)-1,10-diaza-4,7,13,16-tetraoxacyclooctadecane (0.2 mmol) in 2 ml water was added so much LiOH that the pH reached the value 11. Then calcium sulphate (15 mg, 0.11 mmol) was added at room temperature under stirring. The calcium sulphate solid dissolved almost instantaneously. Thereafter a further amount of calcium sulphate solid (13 mg, 0.096 mmol) was added. The resultant mixture was stirred but no clear solution was obtained. Upon the addition of a further amount of 16 mg 1,10-bis(phosphonomethyl)-1,10-diaza-4,7,13,16-tetraoxacyclooctadecane (0.04 mmol) the mixture became clear almost immediately. Thus the phosphono compound had been loaded up to 87%.

EXAMPLE 5

(a) The vessel was charged with barium sulphate (0.45 mmol) and a solution of 1,10-diaza-4,7,13,16-tetraoxacyclooctadecane (0.1 M), sodiumphosphite (0.2 M) and 37% formaldehyde (0.2 M) in 1.5 ml water. The reaction mixture was kept under stirring at ambient temperature during 24 hours. A sample drawn after settling of the suspension contained equal amounts of dissolved barium and dissolved sulphate. The efficiency of the in situ prepared sodium salt of 1,10-bis(phosphonomethyl)-1,10-diaza-4,7,13,16-tetraoxacyclooctadecane (calculated as the amount of BaSO4 (mole) dissolved per mole of 1,10-diaza-4,7,13,16-tetraoxacyclooctadecane charged) was 3.1%. It should be noted that the efficiency of 1,10-diaza-4,7,13,16-tetraoxacyclooctadecane under the same conditions amounts to 0.4%. The experiment was repeated at a temperature of about 70° C. The efficiency of the in situ prepared sodium salt had increased to 5.7%, calculated on the amount of BaSO4 (mole) dissolved per mole of 1,10-diaza-4,7,13,16-tetraoxacyclooctadecane.

(b) A crude reaction mixture obtained by reacting 1,10-diaza-4,7,13,16-tetraoxacyclooctadecane (0.1 M), phosphorous acid (0.2 M) and formaldehyde (0.4 M) in acidic medium (6 N HCl) to pH = 11 was used after the addition of an excess of lithium hydroxide as the "macrocyclic polyether". The efficiency on dissolving solid barium sulphate (0.3 mole per liter) at 20° C. after 24 hours under standard conditions as described in Example 1b was 49% (calculated on 1,10-diaza-4,7,13,16-tetraoxacyclooctadecane charged, indicating a yield of 75%).

In the cleaning method according to the invention, the (aqueous) cleaning compositions adapted for dissolving solids, especially barium sulphate are contacted with the surfaces to be cleaned for a period of time sufficiently long to remove at least a portion of the solid (barium sulphate scale) on said surfaces. Hereby, the composition may be circulated over the surfaces to be cleaned. Thus, when cleaning equipment in a well, the composition may be circulated through the tubular goods in the well, such as by being pumped down through the production tube and being returned to the surface through the annular space between the production tubes and the casing (or vice versa). Also, the composition may be pumped down through the production tubing and into the formation, thereby cleaning the well and the formation pore space by dissolving barium sulphate present therein while flowing along the surfaces that need cleaning. The spent composition of such once-through-dynamic wash procedure is later on returned to the surface by the fluids that are produced through the well after the cleaning operation. In an alternative manner, the cleaning composition may be applied batchwise. The composition is then pumped down in the well and optionally in the pore space of the formation parts to be cleaned and kept in contact in non-flowing condition with the surfaces that are covered with barium sulphate scale, over a period of time sufficiently long to dissolve at least a considerable part of said scale. It is also possible to pump down through the production tubing and into the formation the reactants (the macrocyclic polyether according to formula I, the hypophorous acid and the compound according to formula III, in particular 1,10-diaza-4,7,13,16-tetraoxacyclooctadecane, phosphorous acid and aqueous solution of formaldehyde) which cause in situ formation of the salt of the macrocyclic polyether according to formula I which will then exert its cleaning activities under the prevailing conditions. Also crude reaction mixtures can be pumped down through the production tubing and into the formation. If desired, the cleaning composition, or portions thereof, in which barium sulphate has been dissolved can be acidified to obtain the macrocyclic polyether according to formula I so that it can be recovered and reused.

What is claimed is:

1. A process for dissolving solid barium sulfate in or around a well in a location into which fluid can be flowed, which process comprises:

flowing into said well and into contact with the barium sulfate an aqueous solution consisting essentially of water, a phosphomethyl and amino-substituted macrocyclic polyether and sufficient dissolved alkaline, inorganic, alkali metal or ammonium compound to provide a pH of at least about 8; and, using as said polyether a compound of the formula

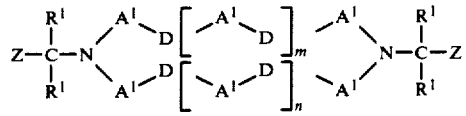

wherein each $A^1$, which may be the same or different, represents a hydrocarbon radical of up to 12 carbon atoms and each D, which may be the same or different, represents an oxygen or sulphur atom or a hydrocarbon radical having up to 6 carbon atoms or a group N-R, representing a hydrogen atom or a hydrocarbon radical having up to 12 carbon atoms, a hydrocarbon sulphonyl radical having up to 12 carbon atoms, an alkoxycarbonylmethylene radical having up to 4 carbon atoms or a carboxymethylene radical, at least two of said D members representing an oxygen or a sulphur atom or a group N-R, and each $R^1$, which may be the same or different, represents a hydrogen atom, an alkyl group having up to 6 carbon atoms or a carboxy group, m and n are whole numbers from 0 to 5 inclusive and Z represents a group

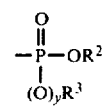

wherein y is 0 or 1 and $R^2$ and $R^3$, which may be the same or different, represent a hydrogen atom or an alkyl group or a lithium, sodium, potassium or ammonium ion.

2. The process of claim 1, wherein each $A^1$ represents a hydrocarbon radical having in the range of from 2 to 6 carbon atoms or a 1,2-phenylene radical, D represents an oxygen or a sulphur atom or a group N-R, R representing a hydrogen atom, an alkyl group of up to 6 carbon atoms, a hydrocarbon sulphonyl radical of up to 6 carbon atoms or an alkoxycarbonylmethylene radical having up to 4 carbon atoms or a carboxymethylene radical; at least 4 of the said D members representing oxygen atoms and/or groups N-R; and each $R^1$ represents a hydrogen atom, an alkyl group having up to 4 carbon atoms or a carboxy group; m and n are 1 or 2; and Z represents a group

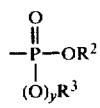

wherein y is 0 or 1 and $R^2$ and $R^3$ represent a hydrogen atom or an alkyl group of up to 6 carbon atoms or a lithium, sodium, potassium or ammonium ion.

3. The process of claim 2, wherein each $A^1$ represents an ethylene, diethylene, triethylene or tetraethylene radical; D represents an oxygen atom or a group N-R, R representing an alkyl group of up to 4 carbon atoms a hydrocarbon sulphonyl radical of up to 4 carbon atoms or a methoxy- or ethoxycarbonyl radical; at least 4 of the said D members representing an oxygen atom; and each $R^1$ represents a hydrogen atom or a methyl or ethyl group; m and n are 1 or 2; and Z represents a group

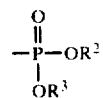

wherein $R^2$ and $R^3$ both represent a hydrogen atom or a lithium, sodium, potassium or ammonium ion.

4. The process of claim 2, wherein each $A^1$ represents an ethylene, diethylene, triethylene or tetraethylene radical; D represents an oxygen atom or a group N-R, R representing an alkyl group of up to 4 carbon atoms, a hydrocarbon sulphonyl radical of up to 4 carbon atoms or a methoxy- or ethoxycarbonyl radical; at least 4 of the said D members representing an oxygen atom; and each $R^1$ represents a hydrogen atom or a methyl or ethyl group; m and n are 1 or 2; and Z represents a group

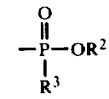

wherein $R^2$ and $R^3$ both represent a hydrogen atom or a lithium, sodium, potassium or ammonium ion.

5. The process of claim 1 wherein $A^1$ represents an ethylene radical; D represents an oxygen atom; and each $R^1$ represents a hydrogen atom or a methyl or ethyl group; m and n are both 1; and Z represents a group

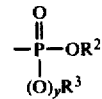

wherein y is 0 or 1, and $R^2$ and $R^3$ both represent a hydrogen atom or a lithium, sodium, potassium or ammonium ion.

* * * * *